(12) United States Patent
Panizzi et al.

(10) Patent No.: US 10,595,794 B2
(45) Date of Patent: Mar. 24, 2020

(54) DEVICES AND METHODS FOR FACILITATING IMAGING OF ROTATING ANIMALS, SPECIMENS, OR IMAGING PHANTOMS

(71) Applicants: AUBURN UNIVERSITY, Auburn, AL (US); MASSACHUSETTS GENERAL HOSPITAL, Boston, MA (US)

(72) Inventors: Peter Panizzi, Auburn, AL (US); Andrew D. Brannen, Auburn, AL (US); Robert D. Arnold, Auburn, AL (US); Matthias Nahrendorf, Boston, MA (US)

(73) Assignees: AUBURN UNIVERSITY, Auburn, AL (US); MASSACHUSETTS GENERAL HOSPITAL, Boston, MA (US)

( * ) Notice: Subject to any disclaimer, the term of this patent is extended or adjusted under 35 U.S.C. 154(b) by 717 days.

(21) Appl. No.: 14/795,632

(22) Filed: Jul. 9, 2015

(65) Prior Publication Data
US 2017/0007192 A1    Jan. 12, 2017

(51) Int. Cl.
*A61B 5/05* (2006.01)
*A61B 6/04* (2006.01)

(52) U.S. Cl.
CPC .................. *A61B 6/0407* (2013.01)

(58) Field of Classification Search
CPC ........................................................ A61B 6/00
See application file for complete search history.

(56) References Cited

U.S. PATENT DOCUMENTS

| | | | |
|---|---|---|---|
| 5,320,069 A | 6/1994 | Anderson et al. | |
| 6,992,762 B2 | 1/2006 | Long et al. | |
| 7,113,217 B2 | 9/2006 | Nilson et al. | |
| 7,486,766 B1 * | 2/2009 | Nagarkar | A61B 6/032 378/19 |
| 8,041,409 B2 | 10/2011 | Leevy et al. | |
| 8,218,836 B2 | 7/2012 | Metaxas et al. | |
| 8,660,631 B2 | 2/2014 | Feke et al. | |
| 2002/0196899 A1 * | 12/2002 | Karellas | A61B 6/06 378/98.8 |
| 2003/0082104 A1 | 5/2003 | Mertelmeier | |

(Continued)

OTHER PUBLICATIONS

Li-Cor, "Pearl Trilogy Small Animal Imaging System". Accessed Aug. 14, 2015. http://www.licor.com/bio/products/imaging_systems/pearl/fieldbrite.html?gclid=Cj0KEQjwhPaqBRDG2uiHzpKLi6ABEiQAk_XXiSFNKDbViUokH2l0GraRgEE1d3GoHtGF8HIN9pNTfV0aAi6A8P8HAQ#sensitivity.

(Continued)

*Primary Examiner* — Joel F Brutus
(74) *Attorney, Agent, or Firm* — Gardner Groff & Greenwald, PC

(57) ABSTRACT

An animal, specimen, or imaging phantom is imaged in precise increments over at least 360 degrees. The animal, specimen, or imaging phantom is supported within a subject holder. The subject holder has an elongated portion or tube for holding securely the animal, specimen or imaging phantom. The subject holder is connected to an actuator motor driver. The actuator motor driver causes the subject holder to rotate at the precise increments, and an image of the animal, specimen, or imaging phantom is captured at each increment. The subject holder limits movement of the subject being imaged at each increment.

27 Claims, 10 Drawing Sheets

(56) References Cited

U.S. PATENT DOCUMENTS

| | | | |
|---|---|---|---|
| 2004/0102705 A1 | 5/2004 | Zan et al. | |
| 2005/0175538 A1* | 8/2005 | Coquoz | G01J 1/42 424/9.2 |
| 2006/0064000 A1 | 3/2006 | Vizard et al. | |
| 2007/0238946 A1* | 10/2007 | Chiodo | A01K 1/0613 600/407 |
| 2008/0049893 A1 | 2/2008 | Bartzke et al. | |
| 2008/0072836 A1* | 3/2008 | Chiodo | A61D 3/00 119/417 |
| 2009/0114825 A1* | 5/2009 | Beekman | G01T 1/1611 250/363.02 |
| 2010/0022866 A1* | 1/2010 | Feke | A61B 5/0059 600/407 |
| 2010/0022872 A1 | 1/2010 | Stearns et al. | |
| 2010/0078576 A1* | 4/2010 | Ntziachristos | A61B 5/0073 250/459.1 |
| 2010/0198047 A1* | 8/2010 | Zagorchev | A61B 6/04 600/411 |
| 2011/0092813 A1* | 4/2011 | Cable | A61B 5/0059 600/427 |
| 2011/0150177 A1* | 6/2011 | Nielsen Groot | A61B 6/107 378/20 |

OTHER PUBLICATIONS

PerkinElmer, IVIS Series Pre-clinical in Vivo Imaging Systems. Accessed Aug. 14, 2015. http://www.perkinelmer.com/catalog/category/id/ivis%20series.

* cited by examiner

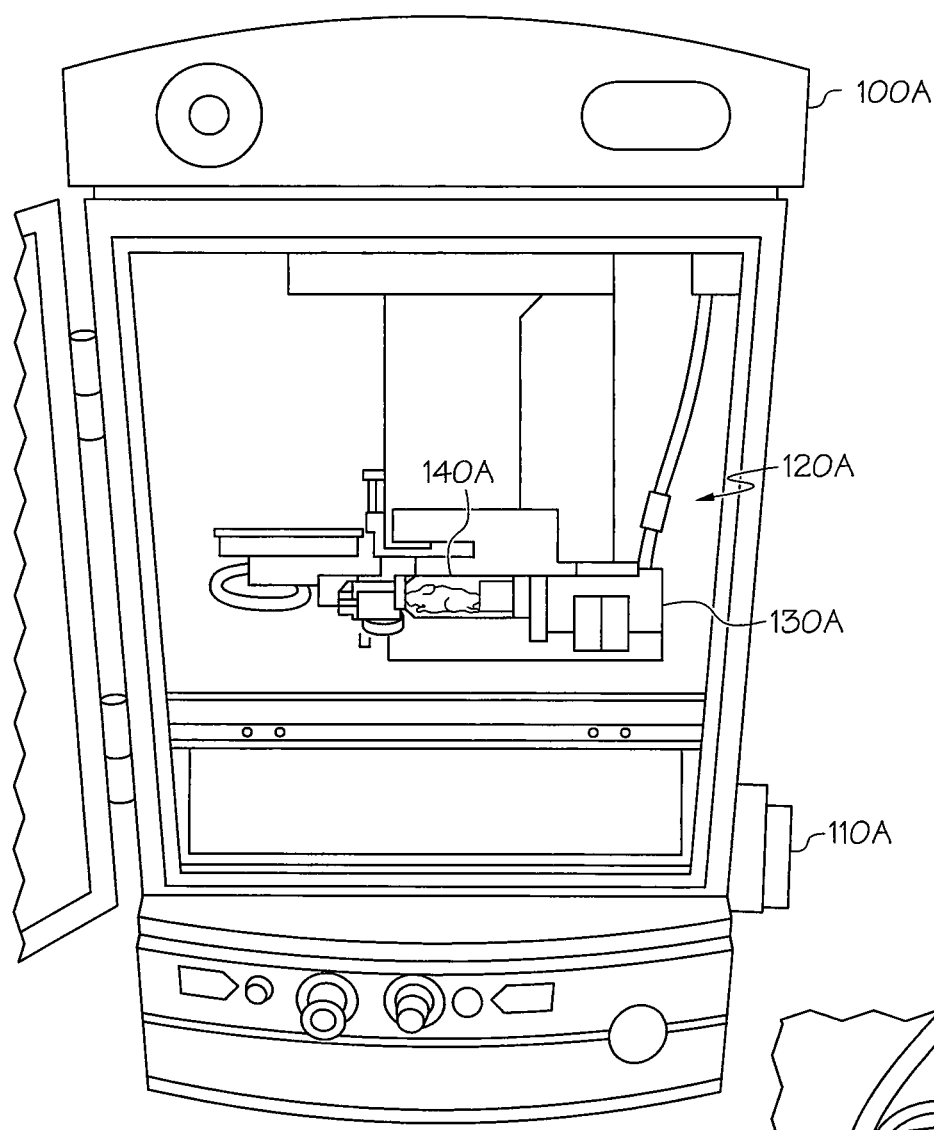
FIG. 1A
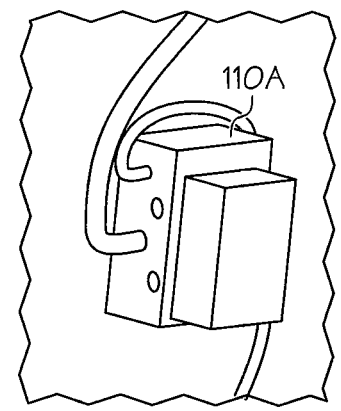
FIG. 1A(1)

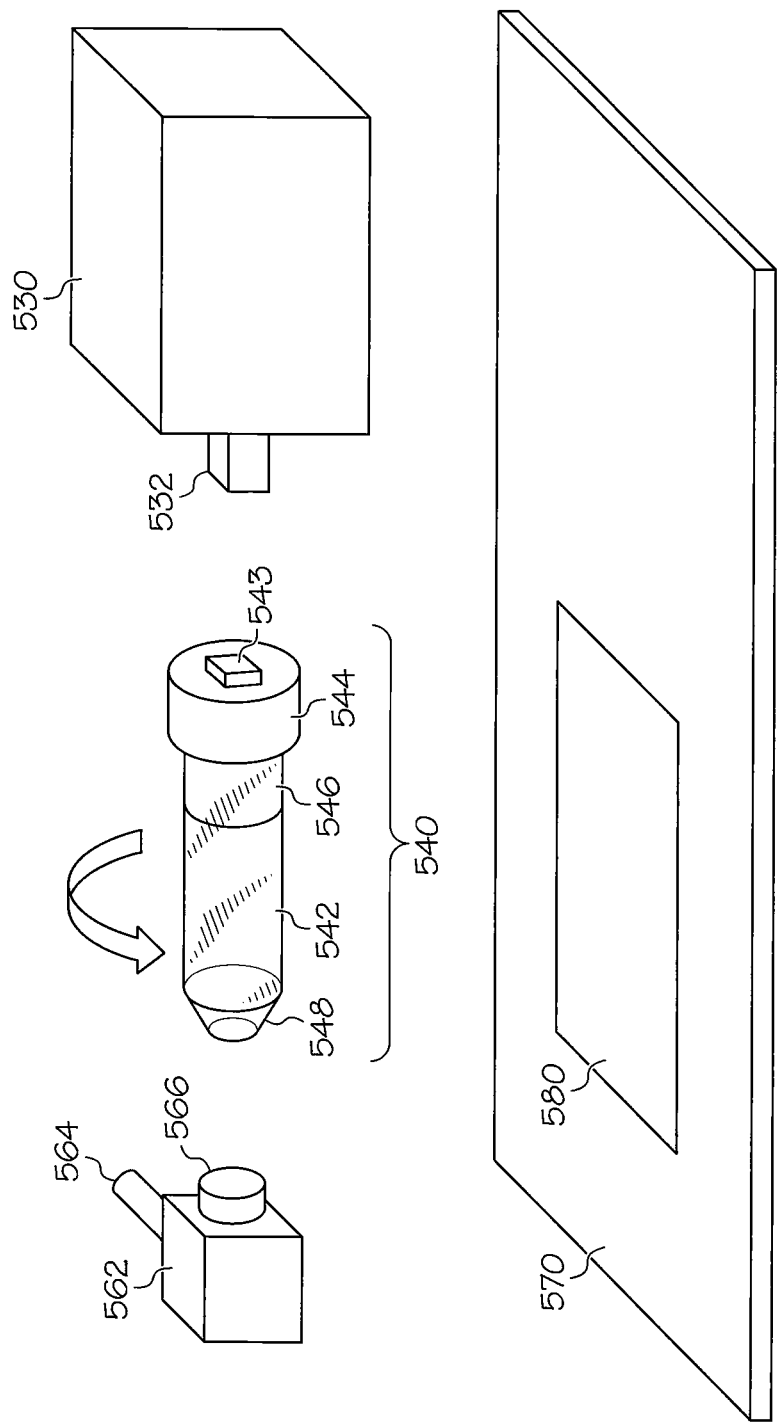

DEVICES AND METHODS FOR FACILITATING IMAGING OF ROTATING ANIMALS, SPECIMENS, OR IMAGING PHANTOMS

TECHNICAL FIELD

The present invention relates generally to the field of imaging, and more particularly to the field of imaging of animals, specimens, or imaging phantoms in a rotational manner.

BACKGROUND

Molecular imaging is gaining popularity in the scientific community as a means of tracking the progression of disease in animals that may also occur in humans. Techniques for imaging include, e.g., X-ray imaging, optical imaging (namely bioluminescent and fluorescent), photo-acoustic imaging, etc. Using such techniques, snapshots of disease states can be collected to monitor the development of abnormalities, such as tumors, in animals over time. Planar imaging modalities acquire images in two-dimensional (2D) space, but the utility of such imaging is hampered by variability created by the total signal intensity in given regions of interest due to the position of the target with respect to the detector. Signal intensity from the target being imaged is related to multiple factors including, but not limited to, the distance and relationship of the signal source to the detector or cooled charge-coupled device (CCD) camera and the location of the signal within the animal.

As light passes through tissue, it scatters due to the inherent absorption properties of blood, muscle, and fat. Thus, tissue acts as a non-homogenous medium for light propagation. Scattering of light doubly affects fluorescence imaging methods, wherein a probe located within an animal must receive enough energy from this diffuse excitation light beam to allow it reach the excited state and produce emitted photons of light which are seen at a Stokes shifted wavelength. As such, both excitation and emission light scatter as they travel to and from the target. As a result, the orientation of the internal target and the CCD camera or detector is a critical determinant of signal intensity, as the more tissue that the light must transverse through, the more the diffusion and loss of signal caused.

To address this problem, researchers often acquire images from multiple orientations of the subject in order to more accurately localize the source of the signal, e.g., an optical signal (bioluminescent/fluorescent signal). The term "subject" will heretofore be used to denote a collection of potential objects being imaged including but not limited to either small animals, tissues, bone, and/or imaging phantoms. However, this manual manipulation of the subject relative to the camera only allows for a typical maximum of four orientations (dorsal, ventral, and each sagittal), and is often not easily reproducible in the same subject, e.g., mouse, monitored over a span of week to months. As a result, these changes in orientation are inherently subjective.

There is distinct advantage to being able to understand the source of a signal in an animal from all angles to eliminate inherent biases. Researchers have been forced to flip and reposition an animal for each image acquisition. This is a tedious process that expands logarithmically the time required of the animal to be under anesthesia, thus threatening the animal's health.

Other imaging modalities, such as fluorescence molecular optical projection, photo-acoustic/opto-acoustic, and positron emission tomographies, have been developed in an attempt to alleviate some of these inherent scattering problems that hamper in vivo optical imaging. For fluorescence molecular tomography (FMT) and positron emission tomography (PET) these concerns are addressed by multiple detectors or by movement of the detector around the subject, respectively. In the case of FMT and optical projection tomography, the fluorescence derived from the target is reconstructed by use of a trans-light projection to correct for the scatter of the signal, thereby creating a single three-dimensional (3D) image of the signal source in a subject. For PET, FMT and optical projection tomography techniques, specialized instrumentation is required to construct a 3D representation of signal from a phantom (or testing platform) or within an animal. The cost for these systems is exponentially higher than "standard optical imaging devices", forthwith representing the PerkinElmer—IVIS Lumina series, Spectral Imaging—Ami-X, ProteinSimple—AlphaImager HP or FluorChem imagers, or similar top mounted CCD or other detector instruments and thus are frequently unaffordable for many laboratories. Another type of commercially available optical imager is the Bruker/Carestream/Kodak MS In vivo MS FX Pro, In vivo FX Pro or In vivo Extreme imagers, which have a rotational system referred to as Multimodality Animal Rotation System (MARS) (U.S. Pat. No. 8,660,631) that is designed for use with their imagers alone and completely incompatible with above mentioned standard optical imaging devices.

Accordingly, it can be seen that needs exist for a device and method for unobstructed 360 degree imaging of specimens in a simple, inexpensive manner that can be used in these standard optical imaging devices.

It is to the provision of devices and methods for meeting these and other needs that the present invention is primarily directed.

SUMMARY

According to an illustrative embodiment, a device is provided for facilitating imaging of an animal, specimen, or imaging phantom. The device includes a multi-positional actuator motor driver and a subject holder having an elongated portion or tube for holding securely the animal, specimen or imaging phantom. The subject holder is connected to the actuator motor driver, and the actuator motor driver enables the subject holder to be rotated at least 360 degrees at precise increments. The subject holder limits movement of the animal, specimen, or imaging phantom being imaged at each increment.

According to another illustrative embodiment an imaging device is provided for capturing images of an animal, specimen, or imaging phantom. The imaging device includes an imaging chamber, a detector within the imaging chamber for capturing an image of the animal, specimen or imaging phantom, and a multi-positional actuator motor driver within the imaging chamber. The imaging device also includes a subject holder having an elongated portion or tube for holding securely the animal, specimen or imaging phantom. The subject holder is arranged within the imaging chamber and is connected to the actuator motor driver. The actuator motor driver enables the subject holder to be rotated at least 360 degrees at precise increments, and the subject holder limits movement of the animal, specimen, or imaging phantom being imaged at each increment.

According to another embodiment, a method is provide for facilitating imaging of an animal, specimen, or imaging phantom. The method includes supporting the animal, specimen, or imaging phantom within a subject holder having an elongated portion or tube for holding securely the animal, specimen or imaging phantom. The subject holder is connected to the actuator motor driver. The method further includes enabling the subject holder to be rotated by the actuator motor driver at least 360 degrees at precise increments, while the subject holder limits movement of the subject being imaged at each increment.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIGS. 1A and 1B illustrate motorized or actuated devices for facilitating imaging in imaging devices according to illustrative embodiments. FIG. 1A(1) illustrates an exploded view of a control module of the device shown in FIG. 1A.

FIG. 5 illustrates details of portions of a device for facilitating imaging according to illustrative embodiments.

DETAILED DESCRIPTION OF EXAMPLE EMBODIMENTS

Figure 1B:
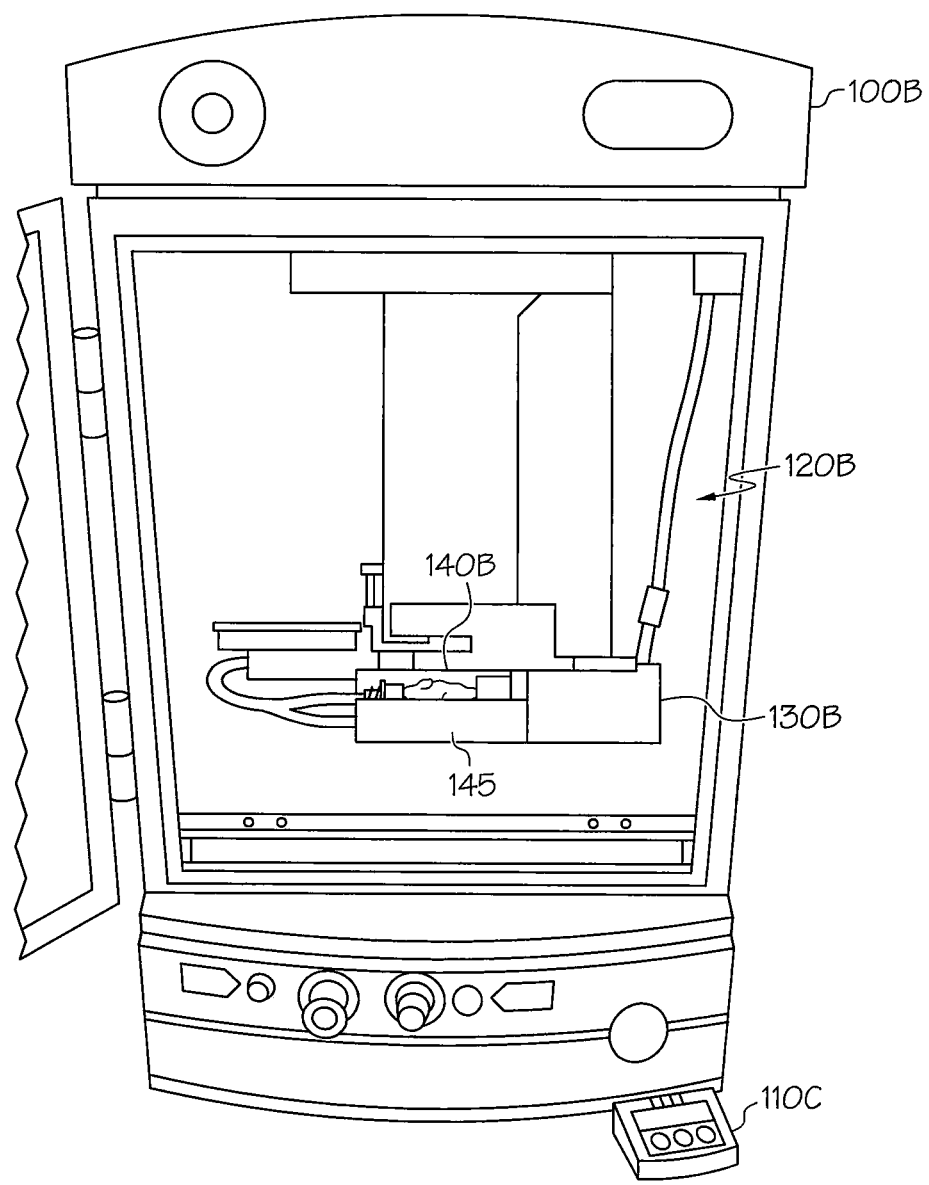

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

According to illustrative embodiments, a device and method are provided that maximize useable information from reporter signals by drastically increasing the number of orientations possible for image acquisition, and altogether remove subjectivity by automating the orientation changing process of the subject being imaged. The device described herein includes an actuating motor that can be programmed to rotate the subject at precise angles around 360 degrees and a subject holder of adjustable dimensions and configurations fitted to the subject maintained in a support structure attached to the actuating motor. The holder is of a sufficient size to restrict the movement of the subject, keeping the subject being imaged in plane and maintaining a critical central axis of rotation of the subject throughout the imaging process. For the applicability of this technology to the use of animals, such as mice, non-invasive imaging of the mice is made possible under general anesthesia, e.g., 1.5% isoflurane per 2 L per min oxygen. The ability to stop and image at specified angles is advantageous, as often imaging requires integration of signals over a discrete time interval. The images acquired from all angles of the animal subject can then be compiled into a video format or potentially reconstructed into a pseudo-3D representation of optical targets in the animal.

According to illustrative embodiments, a spinning or rotating subject in the imaging device allows the user to access 360 degrees around either an object or specimen, such as a live mouse, or in image phantom. The devices and techniques described herein allow users to rotate a subject being imaged at precise degrees of rotation within an imaging chamber with the push of a button, and obtain photographic, fluorescent, bioluminescent, and X-ray images constituting 360 degrees around the subject. Further, the device is compatible with a range of optic based and X-ray imaging devices, such as the PerkinElmer—IVIS Lumina series, Spectral Imaging—Ami-X, ProteinSimple—AlphaImager HP or FluorChem imagers, or similar top mounted CCD or other detector instruments. Once all images are obtained and processed, they can be compiled into a video or "gif" file, giving a pseudo-3D representation of the animal subject.

With reference now to the drawing figures, wherein like reference numbers represent corresponding parts throughout the several views; FIGS. 1A and 1B illustrate imaging devices according to illustrative embodiments.

Referring first to FIG. 1A, the imaging device 100A includes an imaging chamber 120A in which an actuator motor 130A (also referred to herein as an actuator motor driver) capable of causing rotation and a subject holder 140A capable of being rotated are placed. The subject holder 140A includes an elongated tube in which an object, animal, specimen, or imaging phantom to be imaged is placed. Primarily comprised of a restraining tube the circumference of which is of a sufficient size to restrict the movement of the subject being imaged, e.g., an isolated mouse leg bone or femur could be imaged with a small tube filled with agarose while imaging of an entire mouse would require a larger tube with a open end for delivery of anesthesia gas to keep the subject sedated. The tube is optically transparent and keeps the subject being imaged in plane and maintaining a central axis of rotation throughout the imaging process. In addition, the rigid construction of the sides of the tube limits movement of the subject during imaging session. According to an illustrative embodiment, loading of the animal into the holder is done by either (1) loading a sedated mouse into the tube while the tube is vertical and then placing the subject and holder onto the axle of the motor; (2) loading a sedated mouse into the tube resting on an incline by use of a wrist guide wire tool that is secured around the front paws of the animal and using the guide to draw the animal into the subject holder; or by (3) placing the tube on an anesthesia port and allowing the mouse to crawl into the tube to receive the anesthesia gas. In FIG. 1A, the subject holder is depicted as holding a mouse being imaged. However, it should be appreciated that the subject holder may be adapted to hold any size animal, object, specimen, or imaging phantom, wherein the dimensions of the tube would be altered and interchangeable with the size of the subject being imaged.

The subject holder 140A is connected to the actuator motor 130A, and the actuator motor 130A causes the subject holder to rotate around an axis of the elongated tube during imaging. In the embodiment shown in FIG. 1A, the rotation of the actuator motor 130A is controlled by a manual remote controller 110A that is wired to the outside of the imaging chamber 120A. The remote control module 110A allows a user to control the actuator motor 130A to rotate the subject holder in precise increments of 360 degrees without opening the imaging chamber. FIG. 1A(1) shows the control module 110A affixed to the right side of the imaging device.

The actuator motor 130A and the subject holder 140A may be freely positioned within the imaging device. The actuator motor 130A may be held in place by a magnet located to the base or side of the motor driver. The rotation procedure is made precise with the use of the actuator motor 130A, and both the subject holder 140A and the subject being imaged remain in-plane throughout the imaging procedure. The depth of the imaging chamber 120A can allow for the incorporation of more than one of the rotational device assembled in series within the imager for simultaneous acquisition of images of multiple mice. The rotational devices may be linked through interlocking attachments or via sufficient magnets that in both cases would align the rotational devices and enable them to be substantially assembled into one rotational device with, e.g., 2 to 5 rotating subject holders. This is illustrated and explained in more detail with reference to FIG. 4B.

The subject holder 140A is constructed to be attached to the axle of the actuator motor 130A. Also, the subject holder 140A is constructed to allow for the attachment of tubes for anesthesia in order to keep a live specimen being imaged anesthetized throughout the procedure. The actuator motor 130A may be implemented with an existing motor, e.g., a VICI, motor manufactured by Valco Instruments Co. Inc.

FIG. 1B illustrates an imaging device 100B that is similar to the device 100A shown in FIG. 1A. However, as can be seen in FIG. 1B, the subject holder 140B that is connected to the actuator motor 130B within the imaging chamber 120B is supported by a support 145 (shown in and described in more detail with reference to FIG. 4). The support 145 keeps the subject holder 130B from wobbling and vibrating during rotation.

In addition, the actuator motor 130B is controlled by a remote control module 110C that is connected wirelessly to the actuator motor 130B. This allows a user freedom in moving around with respect to the imaging device 100B while controlling rotation of the actuator motor 130B.

Although not shown in FIGS. 1A and 1B in the interest of simplicity of illustration, it should be appreciated that the imaging device may also contain devices for capturing images using, e.g., X-ray imaging, bioluminescence imaging, fluorescence imaging, single positron emission tomography, and PET imaging modalities.

Figure 1C:
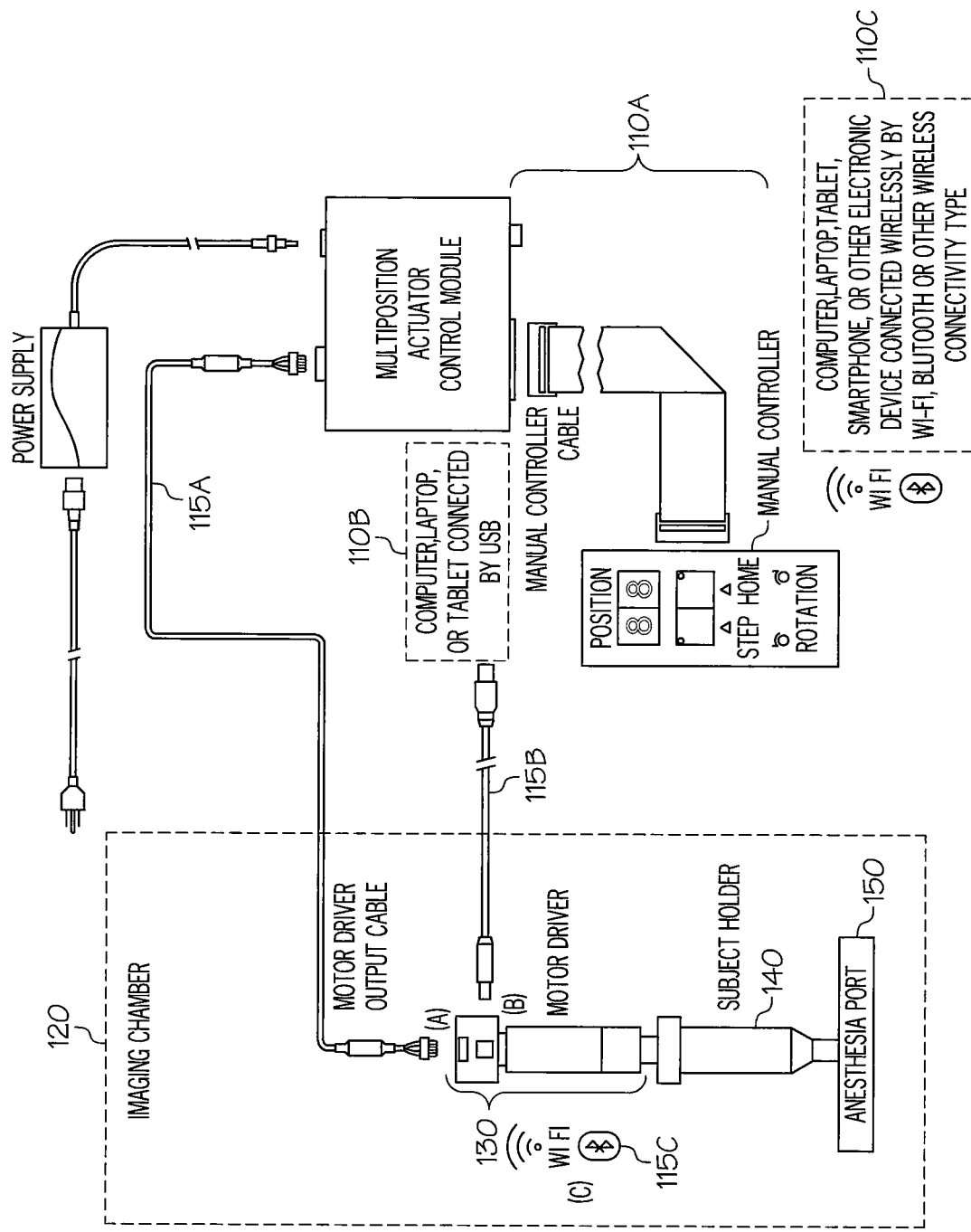
FIG. 1C depicts motorized or actuated devices for use in facilitating imaging in imaging devices with different actuator control modules according to illustrative embodiments.

FIG. 1C illustrates an imaging device with different actuator control modules according to illustrative embodiments. As shown in FIG. 1C, the actuator motor 130 may be connected to a controller mechanism in a variety of different ways. For example, the actuator motor 130 may be connected to a multi-positional actuator control module 110A, such as that shown in FIG. 1A, that is wired to the actuator motor inside of the imaging chamber via a motor driver output cable 115A that is fed through a port into the imaging chamber 120.

As another example, the actuator motor 130 inside of the imaging chamber 120 may be connected to a control module 110B implemented with, e.g., a computer, laptop, or tablet outside of the imaging chamber via a USB connection 115B.

As yet another example, the actuator motor 130 inside of the imaging chamber 120 is connected to a control module 110C, such as that shown in FIG. 1B. This remote control module may be a simple device, such as that shown in FIG. 1B, connected through a wireless connection to a receiver 115C (e.g., WI-FI, Bluetooth, etc). As another option, this control module may be implemented with a more sophisticated device, e.g., a computer, laptop, smartphone, tablet, or other electronic device outside of the imaging chamber 120. In these advanced controls, software can be used to control the degree and increments of rotation for facilitating 360 degree imaging of the subject.

According to an illustrative embodiment, the increments of rotation may be preselected and standardized, such that the user need not adjust the increments of rotation once imaging has started. Alternatively, the increments may be customizable, and the user may adjust the increments as desired during imaging.

According to an illustrative embodiment, a user of a control module, such as the control module 110A, may manually control rotation of the subject holder 140 by the actuator motor 130. As an alternative, a control module, such as the control module 110C, may be used to program rotation of the actuator motor 130, such that once the imaging process is started, the motor causes the subject holder 140 to rotate at the precise increments and imaging occurs at each increment, without requiring further input from the user. This option also allows for automation of the entire imaging process.

Figure 2A:
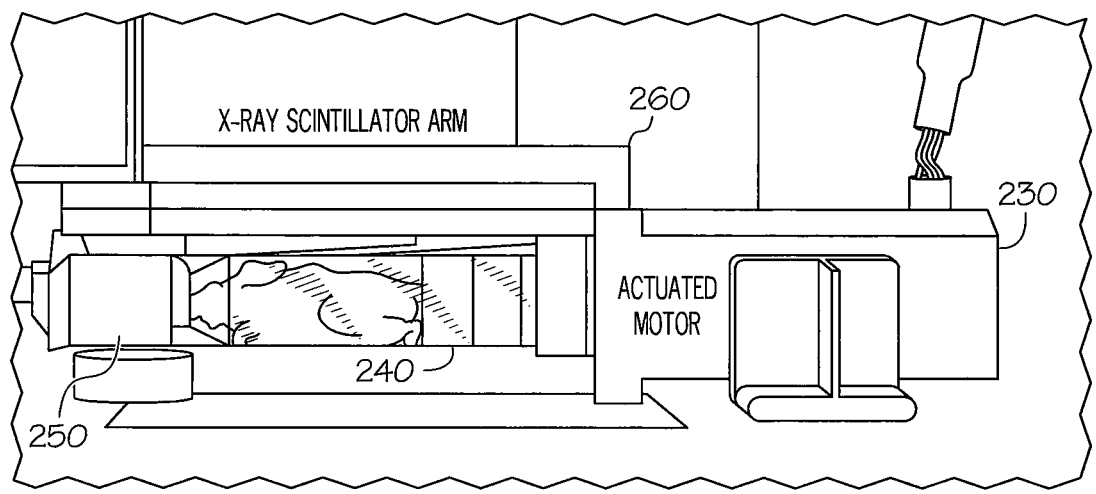
FIGS. 2A and 2B are a side view and a top view, respectively, of a device for facilitating 360 degree imaging of a subject according to a first aspect of the invention.
Figure 2B:
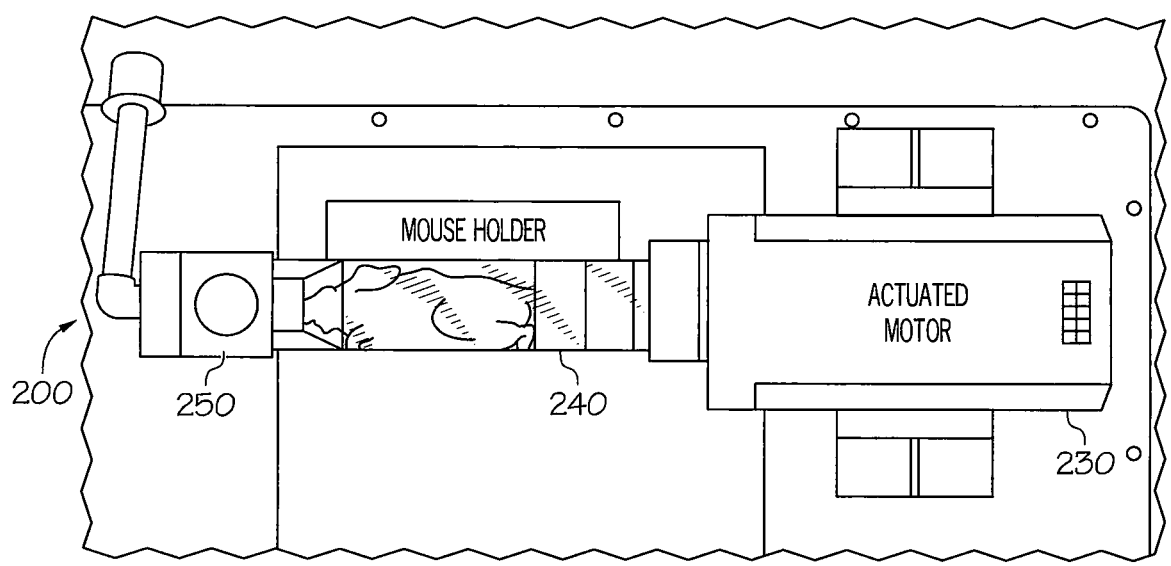

FIGS. 2A and 2B are a side view and a top view, respectively, of a device 200 for facilitating imaging according to a first aspect. As shown in FIGS. 2A and 2B, a subject holder 240 is connected to an actuator motor 230. The subject holder 240 is also connected to an anesthesia port 250.

In the device shown in FIG. 2A, an X-ray scintillator arm containing the phosphor screen 260 is depicted as an example of device, which swings into place in the PerkinElmer IVIS Lumina series instruments during X-ray imaging above the rotational device thereby enabling X-ray imaging. As the subject holder 240 holding the mouse rotates at increments around 360 degrees, 2D X-ray images are captured of the mouse. These images may later be compiled into a three dimensional image or movie to denote a given target probe deposition within the subject, specimen or imaging phantom as described below.

Figure 3A:
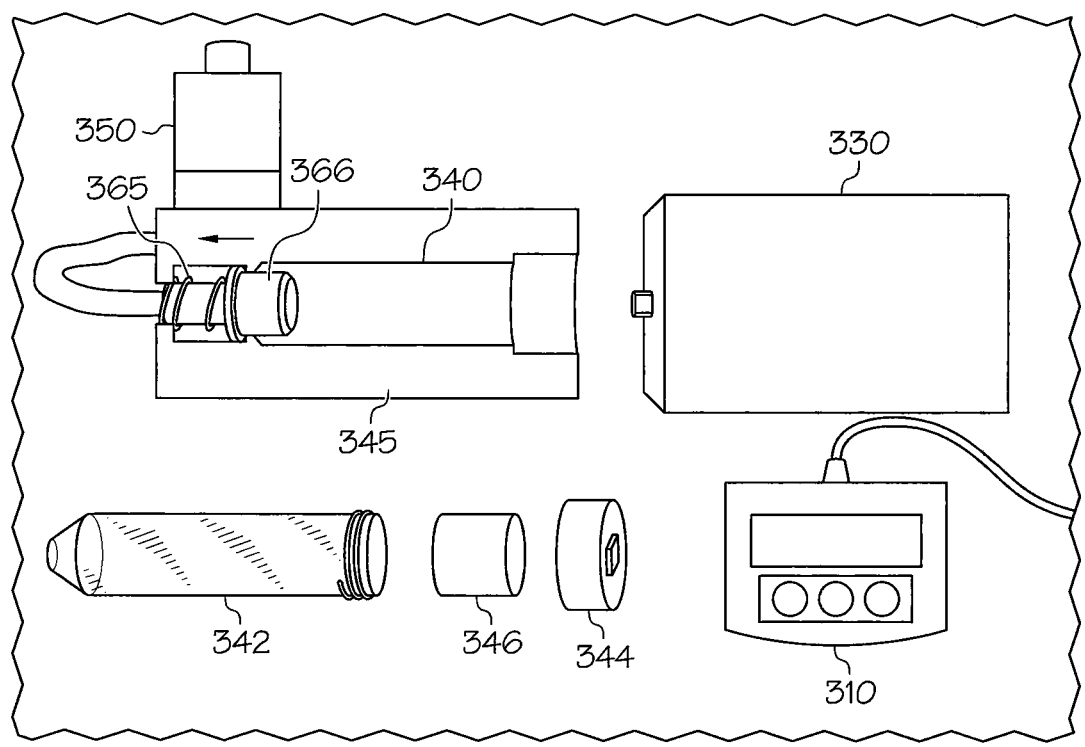
FIGS. 3A and 3B are a separate component view and a top view, respectively, of a device for facilitating 360 degree imaging of a subject according to a second aspect of the invention.
Figure 3B:
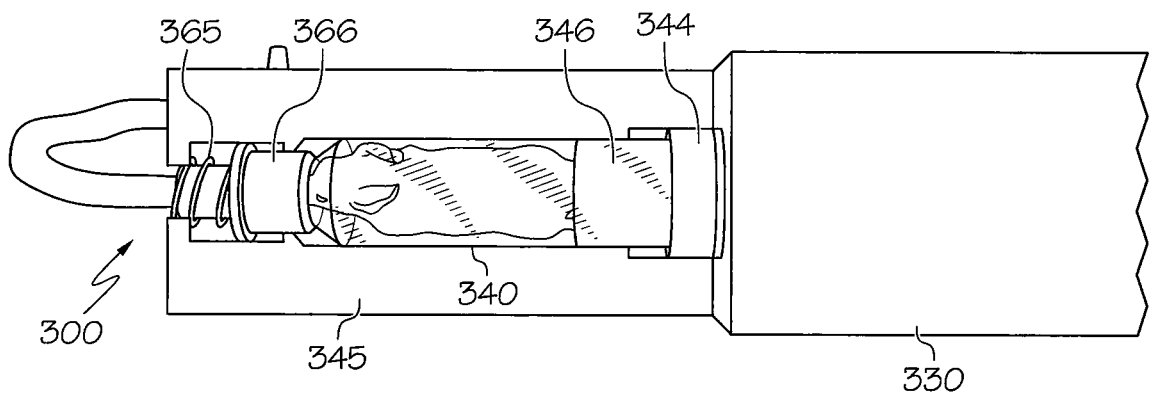

FIGS. 3A and 3B are a side view and a top view, respectively, of a device for facilitating imaging according to a second aspect. Similar to the device shown in FIGS. 2A and 2B, the device 300 shown in FIGS. 3A and 3B includes an actuator motor 330 to which a subject holder 340 is connected. In the device 300 shown in FIGS. 3A and 3B, however, an additional support 345 is added. The support may be implemented with, e.g., a 3D printed stage. The support 345 is fixed within the imaging chamber and minimizes wobbling of the subject holder 340 as it rotates during imaging, resulting in clearer images.

Also shown in FIG. 3A are a controller 310, an animal holder tube 342, an insert 346 made or compressible material, e.g., foam, and a cap connector 344. The animal holder 342, insert 346 and cap connector 344 form the subject holder 340. The insert 346 serves to hold a subject, e.g., a mouse, in place in the animal holder tube 342 during rotation of the subject holder 342. The cap connector 344 facilitates connection of the subject holder 340 to the actuator motor 330. The controller 310 controls the rotation caused by the motor 330 as described above with reference to FIGS. 1B and 1C.

According to this embodiment, the animal holder tube 342 may be lowered into place with the animal loaded inside it. An adaptor 366 is pulled back to allow for entry of the anesthesia gas from the anesthesia port 350. The adaptor 366 is held in position with tension from a spring 365. Once the animal holder 342 is placed on the axis, the spring 365 is released, and this locks the animal holder tube 342 in place, such that it is held at the proximal and distal ends to maintain the central axis while rotation occurs.

Although a controller and details of a subject holder are not shown in FIGS. 2A and 2B, it should be appreciated that a similar controller and subject holder as those shown in FIGS. 3A and 3B may be used in embodiment shown in FIGS. 2A and 2B.

Figure 4A:
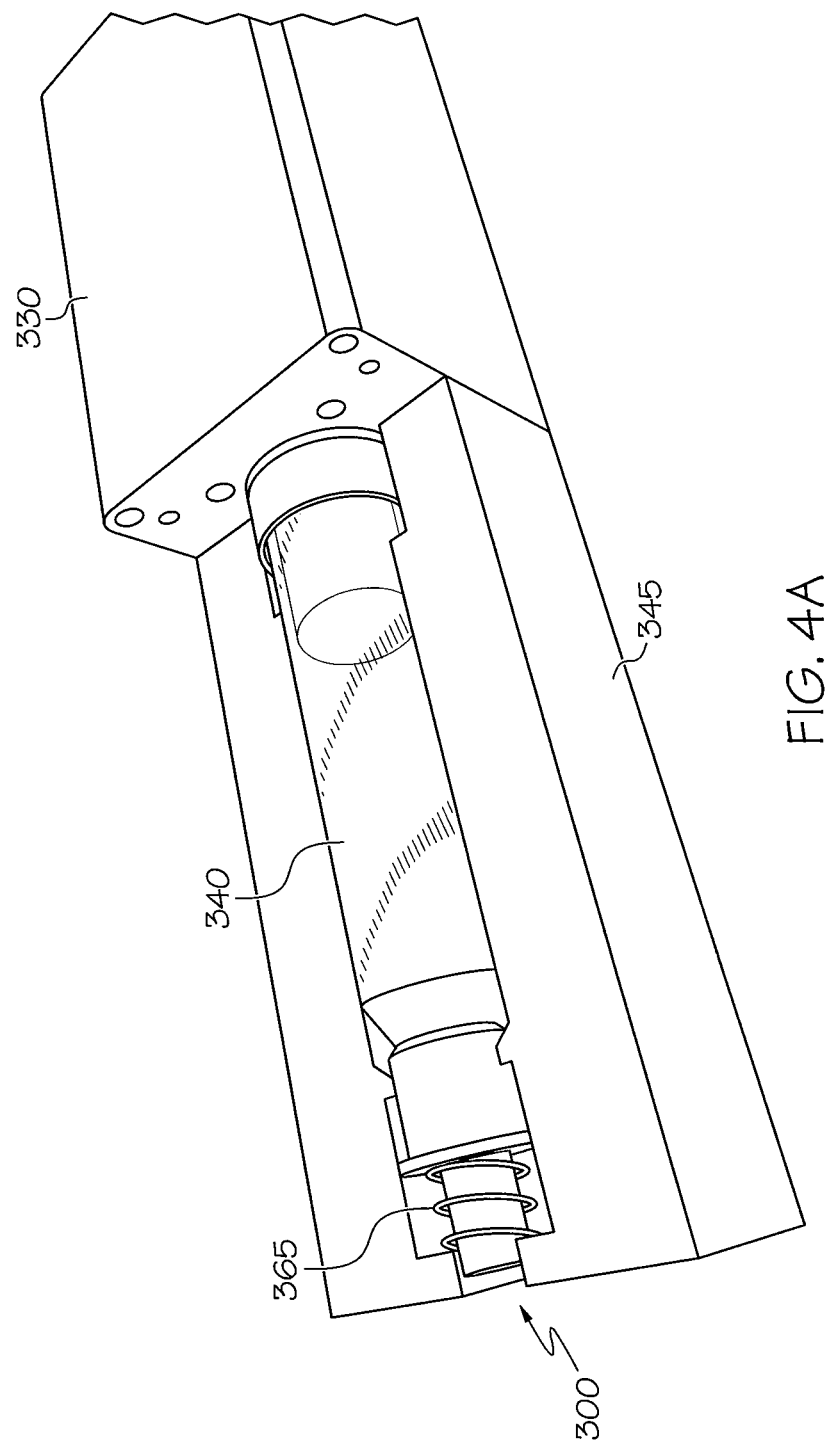
FIG. 4A illustrates a device including a support for holding the rotating subject holder according to an illustrative embodiment.

FIG. 4A illustrates a device for facilitating imaging including a device 345 for supporting a subject holder. As shown in FIG. 4A, the support 345 keeps the subject holder 340 stable while allowing it to be rotated by the actuator motor 330. The support 345 may be formed of plastic, foam, or any other suitable material. As described above, the support may be 3D printed. In this embodiment, the holder platform is static and locked into the motor to minimize vibration caused by the motor and actuated rotation of the subject during imaging.

Figure 4B:
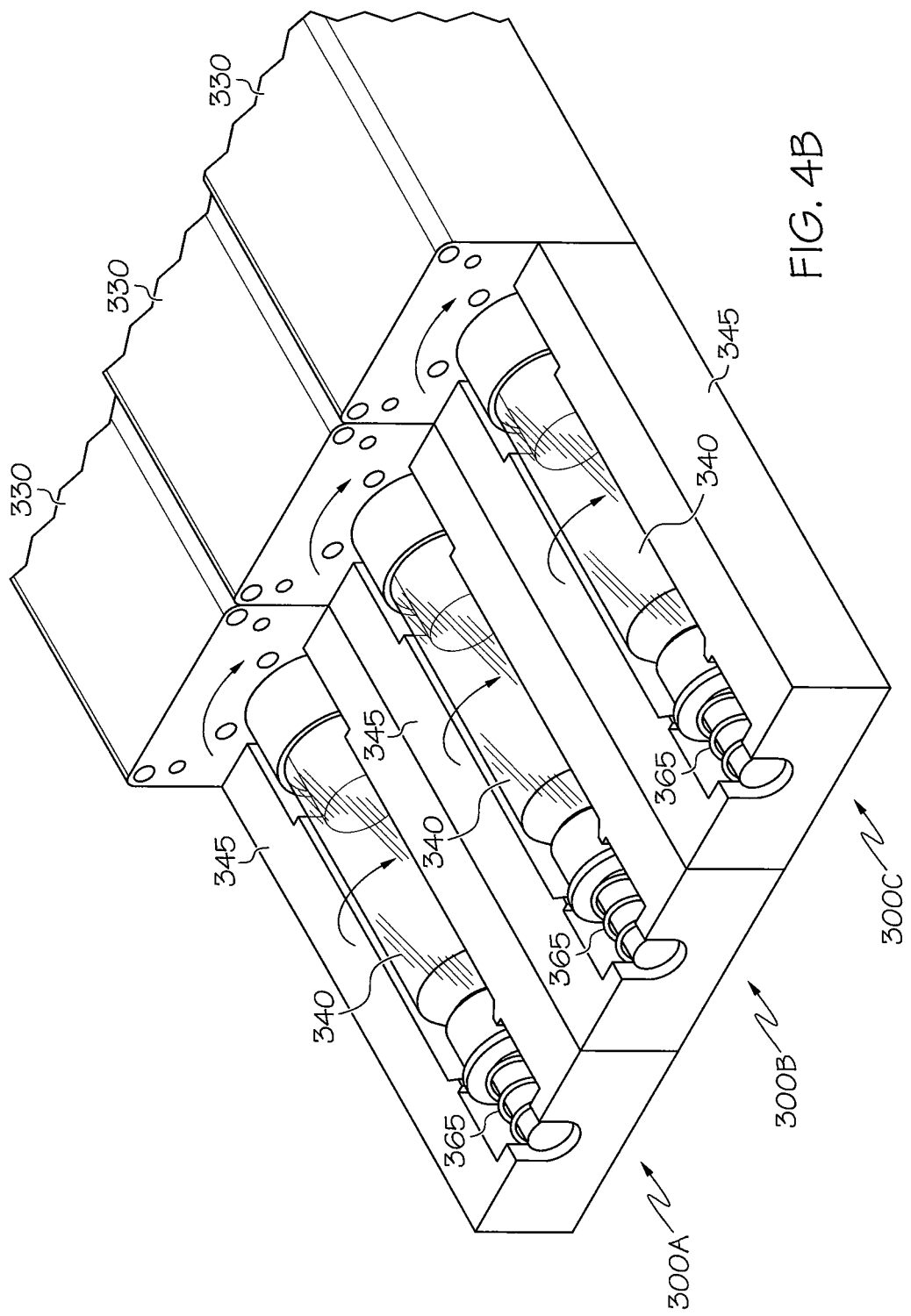
FIG. 4B illustrates multiple devices for facilitating imaging of multiple animals, specimen, or subjects simultaneously.

As noted above, multiple devices, each including a subject holder and an actuator motor, may be included in a single imaging device to facilitate imaging of multiple animals, specimens, or imaging phantoms simultaneously. An example of a configuration of multiple devices is shown in FIG. 4B. Referring to FIG. 4B, three devices 300A, 300B, and 300C are shown for facilitating imaging of animals, specimens, or imaging phantoms. Each device includes an actuator motor 330, a subject holder 340, a support 345, and a spring 365. The actuator motors may cause the subject holders to rotate at the same increments of rotation or at different increments, as desired. The devices may be linked through interlocking attachments or via sufficient magnets that in both cases would align the devices and enable them to be substantially assembled into one device It should be appreciated that any number of such devices may be included within an imaging chamber, to the extent that there is room for the devices to fit. Also, although not shown, it should be appreciated that multiple devices such as that shown in FIG. 5 may also be included in a single imaging device to facilitate imaging of multiple animals, specimens, or imaging phantoms.

FIG. 5 illustrates details of portions of a device for facilitating imaging device according to illustrative embodiments. Referring to FIG. 5, a subject holder 540 includes an open ended nose cone 548 where the head of an animal may be is positioned for imaging. The nose cone 548 includes a hole to allow anesthesia to be delivered to an animal being imaged. The holder 540 further includes a unibody elongated tube 542 that encompasses the nose cone 548. The tube may be made of a material such as glass, acrylic, polypropylene, polystyrene, polyethylene, or similar materials. The subject holder 540 also includes a support 546 made of, e.g., foam. The support 546 snuggly positions the animal being scanned within the tube 542. The subject holder 540 further includes a screw topped cap 543 that tightly secures the nose cone 548, the tube 542, and the support 546. A snap on adapter or port 543 secures the holder 540 to the rotating axle 532 of the actuator motor 530. The actuator motor 530 may be controlled by any of the control mechanisms described above to cause the axle to move such that the subject holder rotates in precise increments around 360 degrees.

Preferably, the tube 542 and other portions of the subject holder 540 are made of inexpensive, disposable materials such that the holder is practical for one use. This prevents cross-contamination between animals being imaged. This is particularly important as the animals being imaged are often immune deficient, due to the tumors or other conditions within the animals which imaging is designed to capture. To maintain sterility of the holder it is expected that these disposable or single use subject holders would be maintained in a sleeve of individually wrapped tubes or blister packs.

Referring again to FIG. 5, a support bracket 562 is provided for the anesthesia port. A connection tube 564 is provided to an isoflurane/anesthesia vaporizer, and a connection coupler 566 is provided between the anesthesia port and the subject holder 540.

A rigid support plate 570 is used to localize the supportive anesthesia port parts 562, 564 and 566 to the subject holder 540 attached to the actuator motor 530. Unlike the embodiment shown in FIG. 4, there is no supportive holder directly beneath the subject holder in this embodiment. Rather, the coupler 566 locks to the plate 570 to minimize vibration. An imaging window 580 allows X-rays to travel from an X-ray source through the subject holder 540 through on their way to the phosphor conversion screen housed in the X-ray scintillator arm used to convert X-ray to photons of light that can be detected by a CCD detector. It should be appreciated that other imaging systems, e.g., bioluminescence imaging systems, may include a similar structure. It should be noted that X-ray capability is dependent on the imaging device itself and is possible for the PerkinElmer IVIS Lumina XRMS and the Spectral Ami-X imager, but not the ProteinSimple—AlphaImager HP or FluorChem imagers, or similar top mounted CCD or other detector based imaging instruments because they lack the underneath X-ray source.

As an illustrative example, a prototype device includes an adapted VICI motor as the actuator motor. In one embodiment, a prototype animal holder includes the following modified parts: 30×II5 mm polystyrene 50 mL conical tube (Denville Scientific) and cap, a 10 mL Lucr-Lok™ tip syringe (BD Medical), and axle coupler included with the actuating motor (VICI). The conical end of the polystyrene tube may be punctured with a heated metal rode in order to create a smooth surface for the mouse snout to be inserted and subsequently connected to the anesthesia system ports. The cap of the conical 544 is modified, for example, by drilling a precise hole in the center. A 10 ml syringe may be cut near the plunger base and modified slightly to hold the axle coupler. The modified cap may then be assembled and fixed into place using super glue. Alternatively, a square shaped hole is drilled into the exact center of the conical cap 544 to generate the 543 port. To accomplish this, a drill press with a $5/16^{th}$ mortising drill bit and mortising chisel (Delta Power Equipment Company, Cat #17-0002) is used to make the necessary square hole for attachment to the square axle 532 on the actuated motor 530. A foam cylinder 546 may be to fit inside of the tube and hold the mouse in place throughout the imaging process. It should be appreciated that this prototype is described for illustrative purposes only, and that other materials and devices may be used for the subject holder and actuator motor. For example, although commercially available polystyrene 50 mL conical tubes with molded markings (Denville Scientific Inc., Cat # C1056), may be used in a similar manner in both embodiments. It is expected that future embodiments would use, a customized plastic mold to improve production consistency and accelerate production.

Figure 6:
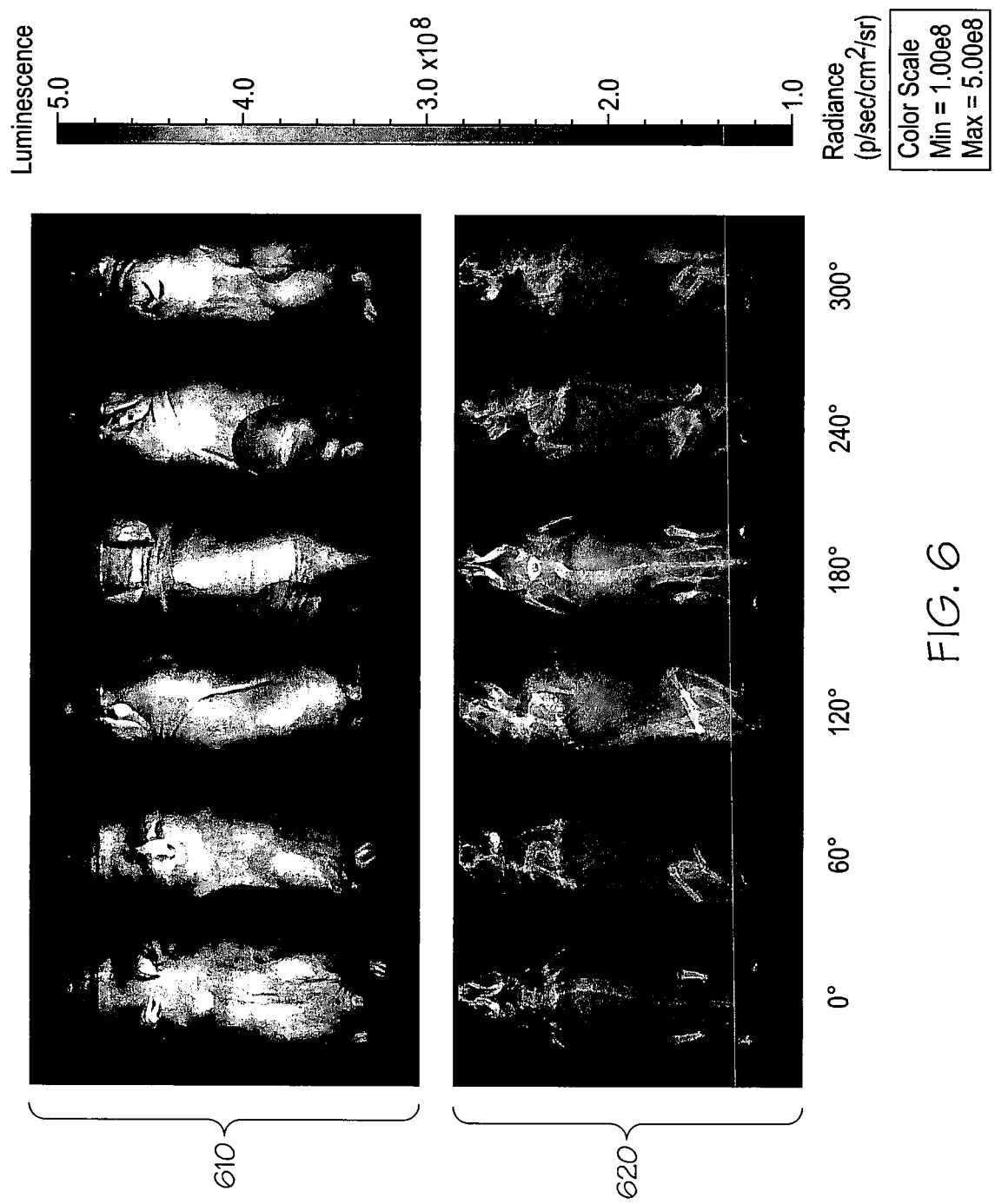
FIG. 6 illustrates examples of images of a live mouse obtained using an imaging device according to illustrative embodiments.

FIG. 6 illustrates examples of images of an object obtained using an imaging device according to an illustrative embodiment. In FIG. 6, images 610 are luminescent images acquired at each increment of rotation and lined up as sequential photographs. Images 620 are X-ray images of the same mouse captured in the images 610, arranged as matching photographs. Although images captured at 60-degree increments are shown in FIG. 6, it should be appreciated that images may be captured at any increment, e.g., 15-degree increments, around 360 degrees. Capturing images in this manner allows for a full-unobstructed view of the mouse.

Figure 7:
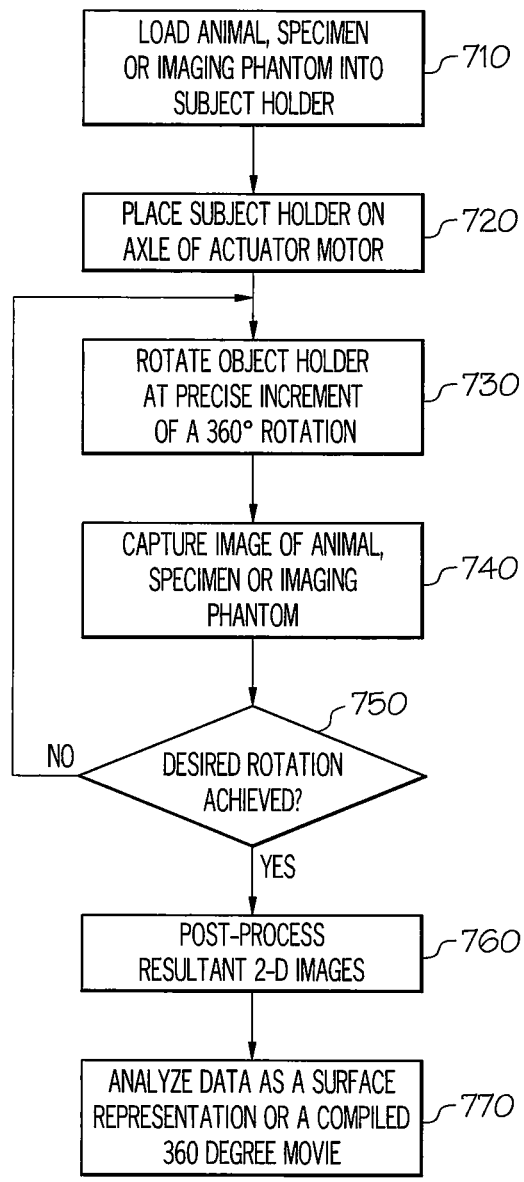
FIG. 7 illustrates a method for imaging according to illustrative embodiments.

FIG. 7 illustrates a method for imaging according to an illustrative embodiment. The method begins at step 710 at which an animal, specimen, or imaging phantom is loaded into a subject holder, e.g., the subject holder 140. In the examples described above, the animal may be a sedated live mouse which is loaded by a user into the subject holder. Alternatively, as described above, a conscious mouse may "self-load" into the subject holder.

At step 720, the subject holder is placed on the axle of the actuator motor, e.g., the actuator motor 130. Once secured to the actuator motor, the subject holder is rotated at a precise increment of 360 degrees at step 730. Next, an image is captured of the animal, specimen, or imaging phantom at step 740.

After the image is captured, a determination is made at step 750, either automatically by a programmed control module or by a user, whether the desired total rotation for imaging has been achieved. For example, it may be desirable to capture images at increments of a 360 degree rotation or increments of a rotation of less than or more than 360 degrees. If, at step 750, it is determined that the desired rotation has not been achieved, the method returns to step 730, and steps 730 and 740 are repeated.

If, at step 750, it is determined that the desired rotation has been achieved, the resultant captured images, which are 2D, are post-processed at step 760 so that they are on the same scale. This may be performed by a computer which may be part of or distinct from a control module, e.g., the control module 110. At step 770, the data is analyzed as a pseudo 3D surface representation or as a compiled 360 degree movie to provide an unobstructed view of the target probe deposition in the animal, specimen or imaging phantom.

According to illustrative embodiments, a devices and techniques are provided that allow imaging of an animal, specimen or imaging phantom by rotation at increments of 360 degrees. Data collected using the devices and techniques described herein are more easily and precisely reproduced than data collected by manually orienting the subject being imaged. In addition, images from multiple orientations can be quickly acquired. This is particular beneficial in the case of an animal being imaged, as it means the amount of time that the animal is under anesthesia is minimized. Another advantage is that the specific degrees of rotation between image acquisitions is known and can be used for post-processing analysis for purposes, such as pseudo-3D reconstruction and region of interest analysis. Further, the subject holder described herein allow for reduction in the cross-contamination associated with a shared animal holder by using a disposable animal holder. The device is flexible in that it can be used with all standard optical imaging systems such as the FluorChem imager from ProteinSimple, or higher end imaging systems like the IVIS Lumina series from PerkinElmer Inc. or Ami-X from Spectral Imaging. In addition, the devices and techniques described herein are compatible with the Bruker/Carestream/Kodak In vivo MS FX Pro, In vivo FX Pro or In vivo Extreme systems. Also, the device described herein may be freely positioned in the respective imagers, and multiple such devices can typically fit within the field of view. This allows for imaging of multiple subject, specimens, or imaging phantoms simultaneously, which speeds up analysis.

While the invention has been described with reference to preferred and example embodiments, it will be understood by those skilled in the art that a variety of modifications, additions and deletions are within the scope of the invention, as defined by the following claims.

The invention claimed is:

1. A device for facilitating imaging of an animal, specimen, or imaging phantom, comprising:
    an imaging chamber
    a support fixed within the imaging chamber;
    a multi-positional actuator motor driver; and
    a subject holder having a first end, a second end, and an elongated portion or tube for holding securely the animal, specimen or imaging phantom, wherein first end of the subject holder is removably connected to the actuator motor driver, and the actuator motor driver enables the subject holder to be rotated at least 360 degrees at prescribed increments, while the subject holder limits movement of the animal, specimen, or imaging phantom being imaged at each increment, and wherein the support fixed within the imaging chamber maintains a stable axis of rotation of the subject holder throughout its incremental rotation.

2. The device of claim 1, wherein the support defines a recess configured to closely receive at least a portion of the subject holder to minimize wobbling or vibration of the subject holder during rotation.

3. The device of claim 1, wherein the subject holder is interchangeable and transparent, and a diameter of the tube is selected from among various diameters to limit movement of the animal, specimen, or imaging phantom being imaged, thereby maintaining a central axis of the animal, specimen, or imaging phantom during rotation.

4. The device of claim 3, wherein the subject holder includes a screw top cap with modification to facilitate attachment of the tube to a base of the actuator motor driver.

5. The device of claim 3, wherein the subject holder further comprises a flexible support within the tube to further limit movement of the animal, specimen, or imaging phantom within the subject holder.

6. The device of claim 3, wherein images captured by imaging at the prescribed increments are singular two-dimensional (2D) images that are subsequently compiled into a pseudo-three dimensional (3D) image and/or 360 degree movie to denote a given target probe deposition within the animal, specimen or imaging phantom, wherein maintaining the central axis of the animal, specimen, or imaging phantom during rotation enables proper post-processing analysis of the 2D images into the pseudo-3D and/or 360 degree movie.

7. The device of claim 1, wherein the subject holder includes an opening for the delivery of anesthesia that enables live small animal imaging.

8. The device of claim 1, wherein the subject holder is disposable and is adapted to snap into place with the animal, specimen, or imaging phantom loaded just prior to the imaging to prevent cross-contaminator between imaging sessions of different animals, specimens, and imaging phantoms.

9. The device of claim 1, wherein the actuator motor driver is controlled by a control module.

10. The device of claim 9, wherein the control module is connected by a hard-wired connection to the actuator motor driver mounted outside an imaging chamber.

11. The device of claim 9, wherein the control module is connected by a wireless connection to the actuator motor driver.

12. The device of claim 1, wherein multiple subject holders are included in an imaging chamber to facilitate simultaneous imaging of multiple subjects, specimens, or imaging phantoms.

13. The device of claim 1, wherein the device facilitates imaging with various imaging techniques including at least one of bioluminescence imaging, fluorescence imaging, X-ray imaging, light-field imaging, photo-acoustic/opto-acoustic imaging, Cerenkov imaging, single positron emission tomography, and positron emission tomography.

14. The device of claim 1, wherein the prescribed increments are customizable or standardized.

15. The device of claim 1, wherein the subject holder further comprises a conical end extending from the elongate portion.

16. The device of claim 1, wherein the subject holder further comprises a compressible insert and a cap connector, the compressible insert configured for placement between the animal, specimen or imaging phantom and the cap connector to hold the animal, specimen or imaging phantom in position during rotation of the subject holder.

17. The device of claim 1, further comprising a spring-biased adaptor configured to detachably engage the second end of the subject holder and retain the subject holder in place for rotation within the imaging chamber and in connection with the actuator motor driver.

18. An imaging device, comprising:
an imaging chamber;
a detector within the imaging chamber for capturing an image of an animal, specimen or imaging phantom;
a subject holder having an elongated portion or tube for securely holding the animal, specimen or imaging phantom, wherein at least a portion of the subject holder is optically transparent to enable imaging therethrough by the detector,
an actuator motor for rotationally driving the subject holder; and
a spring-biased adaptor configured to releasably engage the subject holder and retain the subject holder in connection with the actuator motor driver.

19. The imaging device of claim 18, further comprising a support for the subject holder for minimizing wobbling or vibration of the subject holder during rotation.

20. The imaging device of claim 19, wherein the support defines a recess configured to closely receive at least a portion of the subject holder to minimize wobbling or vibration of the subject holder during rotation.

21. The imaging device of claim 18, further comprising a control module hard-wired to or wirelessly connected to the actuator motor driver to cause the subject holder to rotate at the prescribed increments.

22. The imaging device of claim 18, wherein the detector comprises a scintillator arm comprising a phosphor screen and wherein the subject holder is arranged within the imaging chamber below the phosphor screen.

23. The imaging device of claim 18 wherein the subject holder further comprises a conical end extending from the elongated portion or tube.

24. The imaging device of claim 18, wherein the subject holder further comprises a compressible insert and a cap connector, the compressible insert configured for placement between the animal, specimen or imaging phantom and the cap connector to hold the animal, specimen or imaging phantom in position during rotation.

25. A method for facilitating imaging of an animal, specimen, or imaging phantom comprising:
inserting the animal, specimen, or imaging phantom into a subject holder having an elongated portion or tube for securely holding the animal, specimen or imaging phantom, inserting a compressible insert into the elongated portion or tube, and installing a cap connector to retain the compressible insert and the animal, specimen, or imaging phantom within the elongated portion or tube; and
removably coupling the subject holder with an actuator motor driver; and
rotating the subject holder by operation of the actuator motor driver through at least 360 degrees; and
imaging the animal, specimen, or imaging phantom at prescribed a plurality of rotational increments, while the subject holder limits movement of the subject being imaged at each increment and maintains a consistent central axis of rotation of the animal, specimen, or imaging phantom.

26. The method of claim 25, wherein supporting the animal or specimen within the subject holder comprises loading the animal into the subject holder by guided loading into the tube or conscious self animal loading with the tube connected to an anesthesia source, and the method further comprises controlling the actuator motor driver by a control module to cause the subject holder to rotate at the prescribed increments.

27. The method of claim 25, wherein the images captured by imaging at the prescribed increments are singular two-dimensional (2D) images, and the method further comprises compiling the 2D images into a pseudo-three dimensional (3D) image or movie to denote a given target probe deposition within the animal, specimen or imaging phantom.

* * * * *